(12) United States Patent
Nashman et al.

(10) Patent No.: US 12,290,356 B2
(45) Date of Patent: May 6, 2025

(54) WEARABLE BLOOD ANALYTE MEASUREMENT DEVICE AND METHOD FOR MEASURING BLOOD ANALYTE CONCENTRATION

(71) Applicant: Synex Medical Inc., Toronto (CA)

(72) Inventors: Benjamin Nashman, Toronto (CA); Sunrose Billing, Brampton (CA)

(73) Assignee: Synex Medical Inc., Toronto (CA)

( * ) Notice: Subject to any disclaimer, the term of this patent is extended or adjusted under 35 U.S.C. 154(b) by 0 days.

(21) Appl. No.: 18/371,067

(22) Filed: Sep. 21, 2023

(65) Prior Publication Data

US 2024/0008773 A1 Jan. 11, 2024

Related U.S. Application Data

(63) Continuation of application No. 16/762,010, filed as application No. PCT/CA2018/051398 on Nov. 6, 2018, now Pat. No. 11,793,429.

(Continued)

(51) Int. Cl.
*A61B 5/145* (2006.01)
*A61B 5/00* (2006.01)
(Continued)

(52) U.S. Cl.
CPC ......... *A61B 5/14546* (2013.01); *A61B 5/002* (2013.01); *A61B 5/055* (2013.01);
(Continued)

(58) Field of Classification Search
CPC ..... A61B 5/14546; A61B 5/002; A61B 5/055; A61B 5/14532; A61B 5/4845;
(Continued)

(56) References Cited

U.S. PATENT DOCUMENTS 4,875,486 A 10/1989 Rapoport et al.
5,685,300 A 11/1997 Kuenstner
(Continued)

FOREIGN PATENT DOCUMENTS

ES 1089581 U 9/2013
JP 2004524546 A 8/2004
(Continued)

OTHER PUBLICATIONS

Phuc, H D , et al., "Esign and Construction of Light Weight Portable NMR Halbach Magnet International Journal on Smart Sensing and Intelligent System", International Journal on Smart Sensing and Intelligent Systems. Dec. 1, 2014, vol. 7, No. 4, pp. 1555~1578.
(Continued)

*Primary Examiner* — Carl H Layno
*Assistant Examiner* — Aya Ziad Bakkar
(74) *Attorney, Agent, or Firm* — Jeffrey Schox; Annabel Imbrie-Moore

(57) ABSTRACT

A wearable blood analyte measurement device includes a casing defining an appendage-receiving bore and having an interior volume. A plurality of magnets is within interior volume. The magnets produce a magnetic field in the bore. A nuclear magnetic resonance (NMR) transceiver is supported by the casing and positioned to emit radiofrequency (RF) pulses to and receive NMR signals from the bore. An electronics assembly is within the interior volume and in communication with the NMR transceiver. A power source is in the interior volume and powers the NMR transceiver and the electronics assembly.

19 Claims, 12 Drawing Sheets

Related U.S. Application Data

(60) Provisional application No. 62/638,364, filed on Mar. 5, 2018, provisional application No. 62/584,900, filed on Nov. 12, 2017.

(51) Int. Cl.

| | |
|---|---|
| *A61B 5/055* | (2006.01) |
| *G01R 33/38* | (2006.01) |
| *G01R 33/383* | (2006.01) |
| *G01R 33/3873* | (2006.01) |
| *G01R 33/3875* | (2006.01) |
| *G01R 33/465* | (2006.01) |

(52) U.S. Cl.
CPC ........ *A61B 5/14532* (2013.01); *A61B 5/4845* (2013.01); *A61B 5/681* (2013.01); *A61B 5/742* (2013.01); *G01R 33/3808* (2013.01); *G01R 33/383* (2013.01); *G01R 33/3873* (2013.01); *G01R 33/3875* (2013.01); *G01R 33/465* (2013.01); *A61B 5/6816* (2013.01); *A61B 5/6822* (2013.01); *A61B 5/6826* (2013.01); *A61B 5/6829* (2013.01); *A61B 2560/0214* (2013.01)

(58) Field of Classification Search
CPC .... A61B 5/681; A61B 5/742; G01R 33/3808; G01R 33/383; G01R 33/3873; G01R 33/3875; G01R 33/465
See application file for complete search history.

(56) References Cited

U.S. PATENT DOCUMENTS

| | | |
|---|---|---|
| 6,163,154 A | 12/2000 | Anderson et al. |
| 7,405,567 B2 | 7/2008 | Mcdowell |
| 9,285,441 B1 | 3/2016 | Mcdowell |
| 9,730,635 B2 | 8/2017 | Conrad et al. |
| 9,770,600 B1 | 9/2017 | Demas et al. |
| 10,739,428 B2 | 8/2020 | Mcdowell |
| 10,845,441 B1 | 11/2020 | Mcdowell |
| 11,204,405 B1 | 12/2021 | Mcdowell |
| 2006/0020193 A1 | 1/2006 | Kim et al. |
| 2007/0013374 A1 | 1/2007 | Griswold et al. |
| 2010/0065751 A1* | 3/2010 | Harra .................. A61B 5/14532 250/393 |
| 2012/0197107 A1 | 8/2012 | Griswold |
| 2012/0223705 A1 | 9/2012 | Lowery et al. |
| 2013/0144134 A1* | 6/2013 | Lee .................... A61B 5/14528 600/309 |
| 2013/0200842 A1 | 8/2013 | Takahashi |
| 2014/0081125 A1 | 3/2014 | Zhou et al. |
| 2015/0018638 A1* | 1/2015 | Shames .............. A61B 5/14542 600/301 |
| 2015/0065821 A1 | 3/2015 | Conrad |
| 2015/0377997 A1* | 12/2015 | Zabow ............... A61K 49/1818 324/309 |
| 2016/0011290 A1 | 1/2016 | Iannello |
| 2016/0120438 A1 | 5/2016 | Cima et al. |
| 2016/0206217 A1 | 7/2016 | Rapoport |
| 2016/0270725 A1 | 9/2016 | Gray et al. |
| 2017/0176549 A1 | 6/2017 | Krapf et al. |

FOREIGN PATENT DOCUMENTS

| | | |
|---|---|---|
| JP | 2006023312 A | 1/2006 |
| JP | 2006297110 A | 11/2006 |
| JP | 2013158589 A | 8/2013 |
| JP | 2014503249 A | 2/2014 |
| JP | 2014057862 A | 4/2014 |
| JP | 2015071057 A | 4/2015 |
| JP | 2015510812 A | 4/2015 |
| JP | 2017511464 A | 4/2017 |
| JP | 2018512384 A | 5/2018 |
| RO | 395075 B * | 9/1992 |
| WO | 02088696 A1 | 11/2002 |
| WO | 2012073159 A2 | 6/2012 |
| WO | 2012122462 A2 | 9/2012 |
| WO | 2013140356 A1 | 9/2013 |
| WO | 2015095172 A1 | 6/2015 |
| WO | 2016134275 A1 | 8/2016 |
| WO | 2019143801 A1 | 7/2019 |
| WO | 2020051716 A1 | 3/2020 |

OTHER PUBLICATIONS

Wachowicz, K, et al., "Evaluation of active and passive shimming in magnetic resonance imaging", Research and Reports in Nuclear Medicine. Oct. 15, 2014, vol. 4, pp. 1-12.

* cited by examiner

WEARABLE BLOOD ANALYTE MEASUREMENT DEVICE AND METHOD FOR MEASURING BLOOD ANALYTE CONCENTRATION

CROSS REFERENCES TO RELATED APPLICATIONS

This application is a continuation of U.S. application Ser. No. 16/762,010, now U.S. Pat. No. 11,793,429, filed 6 May 2020, which claims the benefit of 371 of International Application No. PCT/CA2018/o51398 filed 6 Nov. 2018, which claims the benefit of and/or priority from U.S. Provisional Application No. 62/638,364 filed on 5 Mar. 2018, and U.S. Provisional Application No. 62/584,900 filed on 12 Nov. 2017, each of which is incorporated herein by reference in its entirety.

FIELD

This document relates to devices and methods for the measurement of blood analytes. Specifically, this document relates to devices and methods that employ nuclear magnetic resonance (NMR) technology to measure blood analyte concentrations.

BACKGROUND

U.S. Pat. No. 5,685,300 (Kuenstner et al.) discloses a method of non-invasive and in-vitro glucose and cholesterol concentration measurement employing nuclear magnetic resonance (NMR) spectroscopy. The measurement comprises a ratio formed by dividing the area of the resonance of the desired analyte, e.g., glucose or cholesterol, by the area of the water resonance in a spectrum of blood or tissue. In the in-vivo setting, the spectrum is obtained either in linkage with the pulsation of blood or by using a slice selection gradient such as that employed in the magnetic resonance imager. This measurement is then correlated to a traditional serum analyte concentration.

International Patent Application Publication No. WO2012/122462 (Tseng et al.) discloses a system and methods to perform non-invasive, real-time, continuous or episodic molecular detection and quantification of molecular species in a sample or animal or human subject using magnetic resonance. Such systems and methods may be applied to identify and quantify molecular species found in the body, which may be useful for many aspects of medical care including without limitation prenatal diagnosis, detecting deep skin infections, performing cerebral spinal fluid assessment, measuring arterial blood gases, blood glucose, cardiac biomarkers, and creatinine flow rates.

SUMMARY

The following summary is intended to introduce the reader to various aspects of the detailed description, but not to define or delimit any invention.

According to some aspects, a wearable blood analyte measurement device includes a casing defining an appendage-receiving bore and having an interior volume. A plurality of magnets is within the interior volume. The magnets produce a magnetic field in the appendage-receiving bore. A nuclear magnetic resonance (NMR) transceiver is supported by the casing and is positioned to emit radiofrequency (RF) pulses to and receive NMR signals from the appendage-receiving bore. An electronics assembly is within the interior volume and is in communication with the NMR transceiver. The electronics assembly is operable to activate the NMR transceiver to emit an RF pulse to the appendage-receiving bore and to receive an NMR signal from the appendage-receiving bore. A power source is in the interior volume and powers the NMR transceiver and the electronics assembly.

In some examples, the device further comprises a shim system operable to homogenize at least a section of the magnetic field.

In some examples, the shim system includes a dynamic shim system. The dynamic shim system can include an active shim coil within the interior volume and extending around the appendage-receiving bore. The active shim coil can be activatable to homogenize the section of the magnetic field. The electronics assembly can be in communication with the dynamic shim system to activate the active shim coil.

In some examples, the shim system includes a static shim system. The static shim system can include at least one ferromagnetic material within the interior volume.

In some examples, the shim system is operable to homogenize only a section of the magnetic field.

In some examples, the magnets are permanent magnets. The permanent magnets can include neodymium and/or Samarium Cobalt (SmCo).

In some examples, the magnets are arranged in an annulus around the appendage-receiving bore. The annulus can have a radial wall thickness of less than 5 mm. The annulus can have a radial wall thickness of between about 1 mm and about 3 mm.

In some examples, the magnets are arranged in a plurality of rows around the appendage-receiving bore.

In some examples, the magnets are arranged to form a Halbach array.

In some examples, the magnets are arranged in a pattern of alternating cylindrical magnets and bar magnets.

In some examples, the device comprises between 2 and 32 of the magnets.

In some examples, the device comprises 2 magnets arranged on opposed sides of the appendage receiving bore.

In some examples, the magnetic field has a magnetic field strength of less than 1 T. The magnetic field can have a magnetic field strength of between 0.05 T and 0.5 T. The magnetic field can have a magnetic field strength of between 0.1 T and 0.3 T.

In some examples, the casing is non-metallic and non-ferromagnetic. The casing can have an inner section lining the appendage-receiving bore, and the inner section can be non-metallic and non-ferromagnetic.

In some examples, the device further includes a positioning guide for guiding a user in orienting the device at a target orientation. The positioning guide can have a centre-point, and the NMR transceiver can be circumferentially spaced from the centre-point by between 45 degrees and 180 degrees, or by between 80 degrees and 150 degrees.

In some examples the device further includes a heart phase sensor supported by the casing and activatable to sense diastole and systole in a wearer when an appendage of the wearer is received in the appendage-receiving bore. The electronics assembly can be operable to activate the NMR transceiver during diastole, and the RF pulse can be a diastolic RF pulse and the NMR signal can be a diastolic NMR signal. The electronics assembly can be further operable to activate the NMR transceiver during systole to emit a systolic RF pulse to the appendage-receiving bore and receive a systolic NMR signal from the appendage-receiving bore.

In some examples, the power source powers the heart phase sensor.

In some examples, the electronics assembly includes an RF control module in communication with the NMR transceiver. The RF control module can be operable to activate the NMR transceiver to emit the diastolic RF pulse and the systolic RF pulse to the magnetic field. The NMR transceiver can be operable to communicate the diastolic NMR signal and the systolic NMR signal to the RF control module.

In some examples, the electronics assembly further includes a central processing unit (CPU) in communication with the heart phase sensor and the RF control module, The CPU can be operable to receive a heart phase signal from the heart phase sensor, and signal the RF control module to activate the NMR transceiver to emit the diastolic RF pulse during diastole and the systolic RF pulse during systole in response to the heart phase signal received from the heart phase sensor.

In some examples, the RF control module includes (i) an RF transmitter sub-module in communication with the CPU, (ii) an RF receiver sub-module with quadrature detection in communication with the CPU, and (iii) a duplexer in communication with the RF transmitter sub-module, the RF receiver sub-module, and the NMR transceiver.

In some examples, the electronics assembly is further operable to calculate a blood analyte concentration based on the NMR signal.

In some examples, the device further includes a data transmitter within the interior volume and in communication with the electronics assembly. The data transmitter can be operable to transmit the blood-analyte concentration to a secondary device comprising a display. The data transmitter can be operable to transmit the NMR signal to a secondary device. The data transmitter can be a Bluetooth transmitter.

In some examples, the wearable blood analyte measurement device has a weight of less than 50 grams, or of between 1 gram and 20 grams.

In some examples, the RF pulse sequence generates a balanced Steady State Free Precession (b-SSFP) signal. The b-SSFP signal can be generated by rapid, repeated pulses with a constant repetition time.

In some examples, the RF pulse sequence includes a Carr-Purcell-Meiboom-Gill (CPMG) spin echo train. The CPMG can be composed of an initial excitation at the Ernst angle, and repeated 180° pulses with a constant repetition time.

In some examples, the device further includes at least one gradient coil supported by the casing and in communication with the electronics assembly.

In some examples the NMR transceiver comprises a single transceiver coil. In some examples, the NMR transceiver comprises at least one transmitter coil and at least one receiver coil. In some examples, the NMR transceiver comprises at least one of a surface coil and a solenoid coil.

According to some aspects, a kit includes the wearable blood analyte measurement device, and a power charger for charging the power source.

According to some aspects, a method for measuring a blood analyte concentration includes a) using a device worn on an appendage of a user to create a magnetic field within the appendage; b) while the device is worn on the appendage, activating the device to emit an RF pulse to the appendage and receive an NMR signal from the appendage, c) calculating a blood-analyte concentration based on the NMR signal, and d) displaying the blood-analyte concentration on a display.

In some examples, step b. further includes homogenizing at least a section of the magnetic field prior to emitting the RF pulse.

In some examples, the method includes repeating steps b. to d. periodically.

In some examples, the method includes charging a battery of the device prior to step a, and using the battery to power the device during step b. Charging the battery can include inductively charging the battery of the device.

In some examples, the method includes repeating steps b. to d. periodically over a period of between 4 hours and 72 hours on a single charge of the battery.

In some examples, the device is in the form of a ring, and step a. includes placing the ring on a finger of the user.

In some examples, the device includes a plurality of permanent magnets arranged in an annulus, and step a. includes creating the magnetic field using the annulus of magnets.

In some examples, the method includes transmitting the blood-analyte concentration to a secondary device including the display.

In some examples, the blood analyte concentration is a glucose concentration, a cholesterol concentration, a vitamin concentration, an alcohol concentration, a mineral concentration, or a drug concentration.

In some examples, step b. further includes sensing diastole and systole in a user. The RF pulse can be a diastolic RF pulse that is emitted during diastole and the NMR signal can be a diastolic NMR signal. The method can further include emitting a systolic RF pulse to the magnetic field during systole and receiving a systolic NMR signal from the magnetic field. Step c. can include calculating the blood-analyte concentration based on the diastolic NMR signal and the systolic NMR signal.

In some examples, the RF pulse generates a balanced Steady State Free Precession (b-SSFP) signal. The b-SSFP signal can be generated by rapid, repeated pulses with a constant repetition time.

In some examples, the RF pulse includes a Carr-Purcell-Meiboom-Gill (CPMG) spin echo train. The CPMG spin echo train can be composed of an initial excitation at the Ernst angle, and repeated 180° pulses with a constant repetition time.

In some examples, step c. includes employing a T2 filter.

According to some aspects, a wearable blood analyte measurement device includes a casing defining an appendage-receiving bore and having an interior volume. A plurality of magnets is within interior. The magnets produce a magnetic field in the appendage-receiving bore. A nuclear magnetic resonance (NMR) transceiver is supported by the casing and positioned to emit radiofrequency (RF) pulses to and receive NMR signals from the appendage-receiving bore. A heart phase sensor is supported by the casing and is activatable to sense diastole and systole in a wearer when an appendage of the wearer is received in the appendage-receiving bore. An electronics assembly is within the interior volume and is in communication with the NMR transceiver. The electronics assembly is operable to activate the NMR transceiver during diastole to emit a diastolic RF pulse to the appendage-receiving bore and receive a diastolic NMR signal from the appendage-receiving bore, and activate the NMR transceiver during systole to emit a systolic RF pulse to the appendage-receiving bore and receive a systolic NMR signal from the appendage-receiving bore. A power source is in the interior volume and powers the NMR transceiver, the heart phase sensor, and the electronics assembly.

In some examples, the device further includes a shim system operable to homogenize at least a section of the magnetic field. In some examples, the shim system is operable to homogenize only a section of the magnetic field In some examples, the shim system includes a dynamic shim system. The dynamic shim system can include an active shim coil within the interior volume and extending around the appendage-receiving bore. The active shim coil can be activatable to homogenize the section of the magnetic field. The electronics assembly can be in communication with the dynamic shim system to activate the active shim coil.

In some examples, the shim system includes a static shim system. The static shim system can include at least one ferromagnetic material within the interior volume.

In some examples, the magnets are permanent magnets. The permanent magnets can be or can include neodymium and/or Samarium Cobalt (SmCo). The magnets can be arranged in an annulus around the appendage-receiving bore. The annulus can have a radial wall thickness of less than 5 mm, for example between about 1 mm and about 3 mm. The magnets can be arranged to form a Halbach array. The device can include between 2 and 32 of the magnets.

In some examples, the magnetic field has a magnetic field strength of less than 1 T (Tesla). In some examples, the magnetic field has a magnetic field strength of between 0.05 T and 0.5 T. In some examples, the magnetic field has a magnetic field strength of between 0.1 T and 0.3 T.

In some examples, the casing is non-metallic and non-ferromagnetic. In some examples, the casing has an inner section lining the appendage-receiving bore, and the inner section is non-metallic and non-ferromagnetic.

In some examples, the device includes a positioning guide for guiding a user in orienting the device at a target orientation. The positioning guide can have a centre-point, and the NMR transceiver can be circumferentially spaced from the centre-point by between 45 degrees and 180 degrees. For example, the NMR transceiver can be circumferentially spaced from the centre-point by between 80 degrees and 150 degrees.

In some examples, the electronics assembly includes an RF control module in communication with the NMR transceiver. The RF control module can be operable to activate the NMR transceiver to emit the diastolic RF pulse and the systolic RF pulse to the magnetic field. The NMR transceiver can be operable to communicate the diastolic NMR signal and the systolic NMR signal to the RF control module.

In some examples, the electronics assembly includes a central processing unit (CPU) in communication with the heart phase sensor and the RF control module. The CPU can be operable to receive a heart phase signal from the heart phase sensor, and signal the RF control module to activate the NMR transceiver to emit the diastolic RF pulse during diastole and the systolic RF pulse during systole in response to the heart phase signal received from the heart phase sensor.

In some examples, the RF control module includes (i) an RF transmitter sub-module in communication with the CPU, (ii) an RF receiver sub-module with quadrature detection in communication with the CPU, and (iii) a duplexer in communication with the RF transmitter sub-module, the RF receiver sub-module, and the NMR transceiver.

In some examples, the electronics assembly is further operable to calculate a blood analyte concentration based on the diastolic NMR signal and the systolic NMR signal.

In some examples, the device includes a data transmitter within the interior volume and in communication with the electronics assembly. The data transmitter can be operable to transmit the blood-analyte concentration to a secondary device comprising a display, and/or to transmit the diastolic NMR signal and the systolic NMR signal to a secondary device. The data transmitter can be a Bluetooth transmitter.

In some examples, the device has a weight of less than 50 grams. In some examples, the weight is between 1 gram and 20 grams.

According to some aspects, a kit includes the wearable blood analyte measurement device, and a power charger for charging the power source.

According to some aspects, a method for measuring a blood analyte includes a) using a device worn on an appendage of a user to create a magnetic field within the appendage. The method further includes b) while the device is worn on the appendage, activating the device to i) sense systole and diastole in the user; ii) emit a diastolic RF pulse to the appendage during diastole and receive a diastolic NMR signal from the appendage; and iii) emit a systolic RF pulse to the appendage during systole and receive a systolic NMR signal from the appendage. The method further includes c) calculating a blood-analyte concentration based on the systolic NMR signal and the diastolic NMR signal, and d) displaying the blood-analyte concentration on a display.

In some examples, step b) further includes homogenizing at least a section of the magnetic field prior to sub-step ii.

In some examples, the method includes repeating steps b) to d) periodically.

In some examples, the method includes charging a battery of the device prior to step a), and using the battery to power the device during step b). Charging the battery of the device can include inductively charging the battery of the device.

In some examples, the method includes repeating steps b) to d) periodically over a period of between 4 hours and 72 hours on a single charge of the battery.

In some examples, the device is in the form of a ring, and step a) includes placing the ring on a finger of the user. The device can include a plurality of permanent magnets arranged in an annulus to form a Halbach array, and step b) can include creating the magnetic field using the Halbach array.

In some examples, the method includes transmitting the blood-analyte concentration to a secondary device having the display.

In some examples, the blood analyte concentration is a glucose concentration, a cholesterol concentration, a vitamin concentration, an alcohol concentration, a mineral concentration, or a drug concentration.

BRIEF DESCRIPTION OF THE DRAWINGS

The drawings included herewith are for illustrating various examples of articles, methods, and apparatuses of the present specification and are not intended to limit the scope of what is taught in any way. In the drawings.

DETAILED DESCRIPTION

Figure 1:
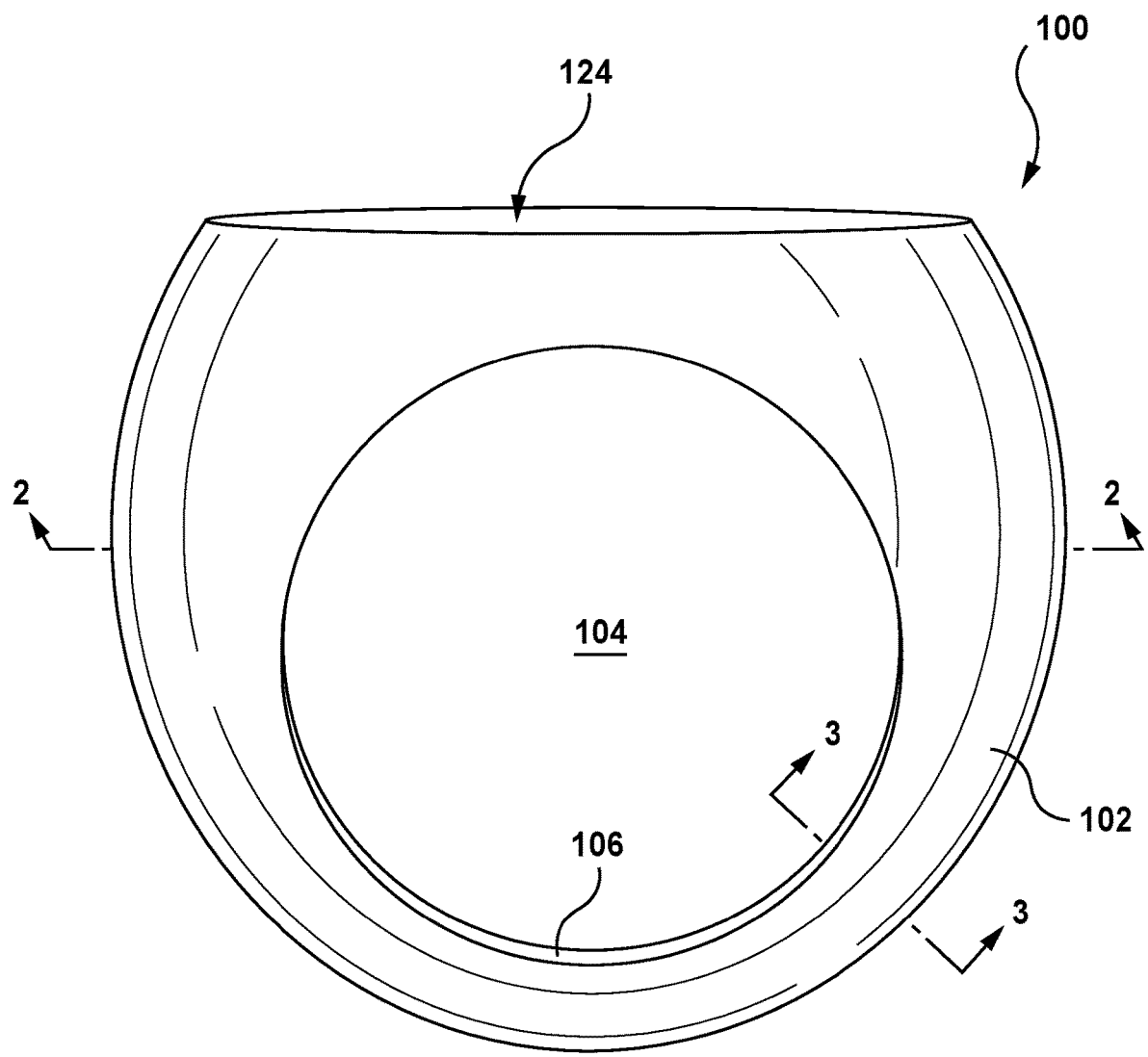
FIG. 1 is a perspective view of an example wearable blood analyte measurement device.

Various apparatuses or processes will be described below to provide an example of an embodiment of the claimed subject matter. No embodiment described below limits any claim and any claim may cover processes or apparatuses that differ from those described below. The claims are not limited to apparatuses or processes having all of the features of any one apparatus or process described below or to features common to multiple or all of the apparatuses described below. It is possible that an apparatus or process described below is not an embodiment of any exclusive right granted by issuance of this patent application. Any subject matter described below and for which an exclusive right is not granted by issuance of this patent application may be the subject matter of another protective instrument, for example, a continuing patent application, and the applicants, inventors or owners do not intend to abandon, disclaim or dedicate to the public any such subject matter by its disclosure in this document.

In general, disclosed herein is a wearable blood analyte measurement device, and related methods. The device may be, for example, a piece of jewelry, such as a ring, a bracelet, an earring, or a necklace. The device employs nuclear magnetic resonance (NMR) technology—i.e. emits radiofrequency (RF) pulses, and receives resulting NMR signals—to determine (or to facilitate the determination of) the concentration of an analyte (such as glucose, cholesterol, a vitamin, alcohol, a mineral, or a drug) in the blood of a wearer. The device can be worn on an appendage (e.g. on a finger, a wrist, a neck, a toe, and earlobe, etc.), in order to create a magnetic field within the appendage, and can be activated to obtain NMR signals from the appendage. The NMR signals can be processed to determine a concentration of the analyte in the wearer's blood.

In general, the device can be used to non-invasively (i.e. without puncturing the skin) determine the concentration of an analyte in the blood of a wearer. This may allow for ease and comfort of use, and can facilitate patient compliance and promote health.

The device may itself process the NMR signals and calculate the blood concentration of the analyte based on the NMR signals, or may transmit the NMR signals to a secondary device (such as, for example, a smart-watch, a smart-phone, a tablet, a computer, or a drug delivery device) that processes and/or calculates the blood concentration of the analyte. The device may itself display the blood concentration of the analyte, or the secondary device may display the blood concentration of the analyte.

The device may be used, for example, by a person having a medical condition in order to monitor that medical condition. For example, the device may be worn by a diabetic wearer in order to monitor their blood-glucose concentration, or may be worn by a person suffering from high cholesterol in order to monitor their blood cholesterol concentration. As an alternative example, the device may be used by law enforcement in order to monitor substance use or abuse in a wearer. For example, the device may be worn in order to monitor the blood alcohol concentration or the concentration of an illicit substance (e.g. THC) in the blood of a wearer. As a further alternative example, the device may be worn in order to promote and/or maintain health and wellness. For example, the device may be worn by a wearer in order to monitor the concentration of a vitamin or mineral in their blood, or the concentration of another indicator of health or wellness. As an alternative example, the device may be worn in order to measure a metabolite of a drug.

The device may be used to measure the concentration of an analyte in a wearer's blood, as opposed to other tissues. This may provide valuable clinical or other information. For example, in the case of a diabetic patient, the concentration of glucose in the blood, as opposed to other tissues, can be of particular concern. In some examples, this is achieved by linking the NMR signals received by the device to the heart phase of the wearer. For example, the device can include a heart phase sensor, such as an LED (light emitting diode) heart rate monitor, that determines diastole and systole in the wearer. The difference in the NMR signals generated during diastole and during systole can be indicative of the concentration of an analyte in a wearer's blood (as opposed to other tissues), and can be used to calculate the concentration of the analyte in the wearer's blood. In other examples, this is achieved by taking advantage of certain unique properties of blood. For example, blood can have a high T2/T1 ratio. Accordingly. the device may employ balanced Steady State Free Precession (b-SSFP) pulse sequences, which are sensitive to tissues/molecules with a high T2/T1 ratio. For further example, since blood is in motion within the body, the device may employ phase contrast magnetic resonance angiography (MRA), in which magnetic resonance signals are sensitive to moving spins. For further example, since blood has a relatively high T2 time, the device can employ a T2 filter, to filter out signals from other tissues.

In some examples, the device can be worn and used over a relatively long period of time, such as hours, days, or more. This can allow for regular and ongoing monitoring of a blood analyte concentration. For example, in the case of a diabetic patient, the device can be worn daily for the duration of the day, and blood glucose concentrations can be determined regularly over the course of the day. Concentrations can be, for example, determined continuously or intermittently (e.g. hourly or more).

The device can be configured to measure one or more specific analytes in a patient's blood. In such examples, since the analyte of concern is known, and it is only the concentration of the analyte that is to be determined, the device does not necessarily require the extremely high magnetic fields required of common NMR devices. For example, NMR machines are often used in laboratories to determine the chemical structure of an unknown compound. This can require magnetic field strengths of 20 Tesla (T) or more. However, in the present example, since it is not necessary to determine the chemical structure of any compound, but merely the concentration of a known compound, a lower magnetic field strength can be used. For example, the device may have a magnetic field strength of less than 1 Tesla (T). Because a lower magnetic field strength is required, the device can be relatively small and light in weight (e.g. small enough and light enough to be worn on a finger). For example, the device may have a weight of less than 50 grams, or less than 20 grams, or between 1 gram and 20 grams.

Referring now to FIG. 1, a first example of a wearable blood analyte measurement device 100 is shown. In the example shown, the device 100 is in the form of a ring, which is wearable on a person's finger. In alternative examples, a wearable blood analyte measurement device may be in the form of a bracelet, a necklace, an earring, or another piece of jewelry or wearable item.

Referring still to FIG. 1, in the example shown, the device 100 includes a casing 102, which supports various other parts of the device 100. The casing 102 defines an appendage-receiving bore 104, in which an appendage of a wearer may sit. In the example shown, wherein the device 100 is a ring, the appendage-receiving bore 104 is for receiving a finger. In alternative examples, an appendage-receiving bore may be for receiving a wrist, an earlobe, a neck, a toe, an ankle, or another body part. The casing has an inner section 106 that lines the appendage-receiving bore.

Figure 2:
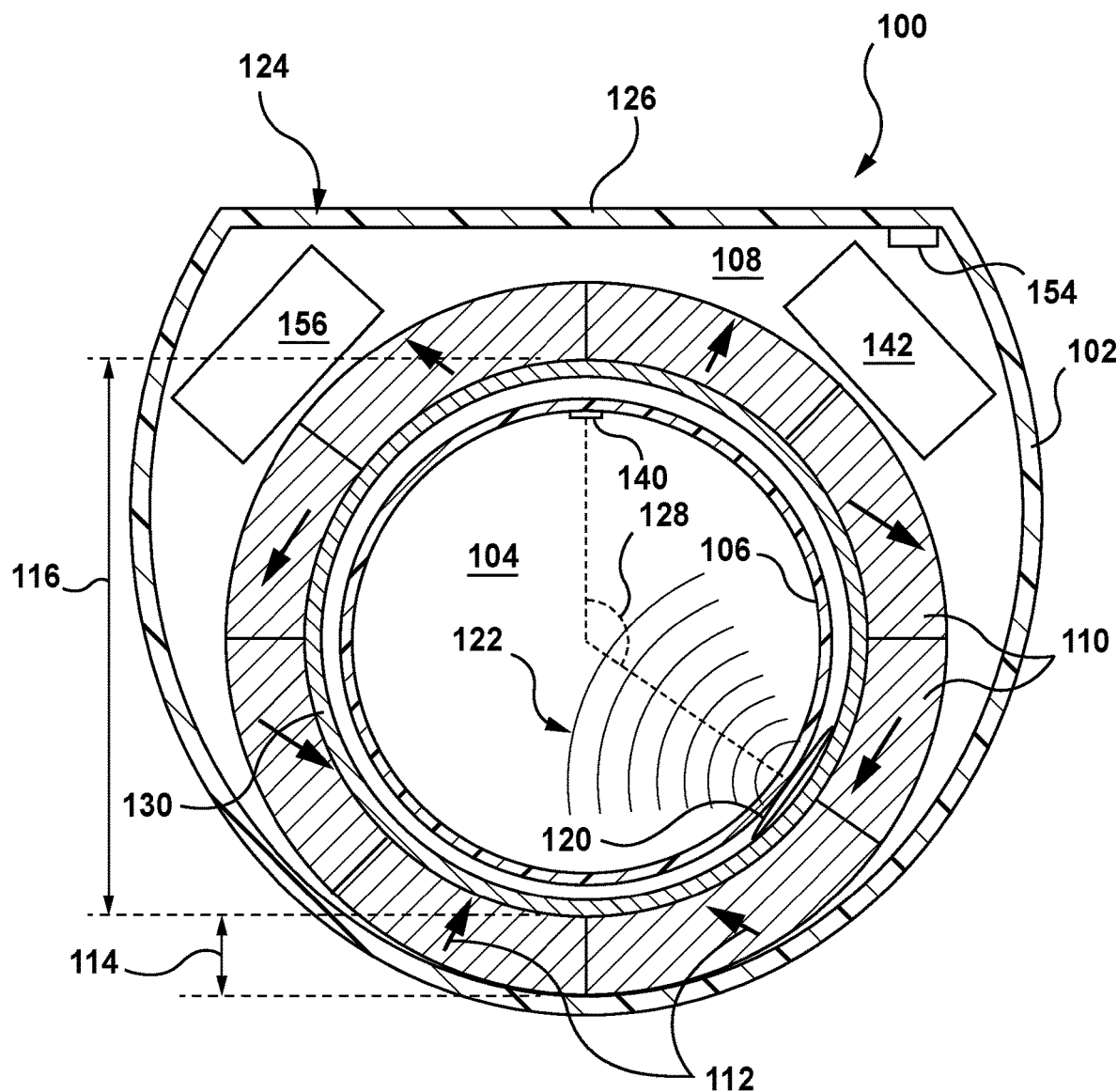
FIG. 2 is a cross section taken along line 2-2 in FIG. 1.

Referring to FIG. 2, in the example shown, the casing 102 has an interior volume 108. As noted above, the casing 102 supports various other parts of the device 100. These other parts may be within the interior volume 108, or exterior to and mounted to the casing 102.

In some examples, the casing 102 is made (in whole or in part) from a non-ferromagnetic and non-metallic material, such as but not limited to a plastic, a ceramic, a wood, a rubber, or a combination thereof. Such non-ferromagnetic and non-metallic materials may prevent, reduce, or minimize the interaction of the casing 102 with the magnetic field of the device 100.

Figure 3:
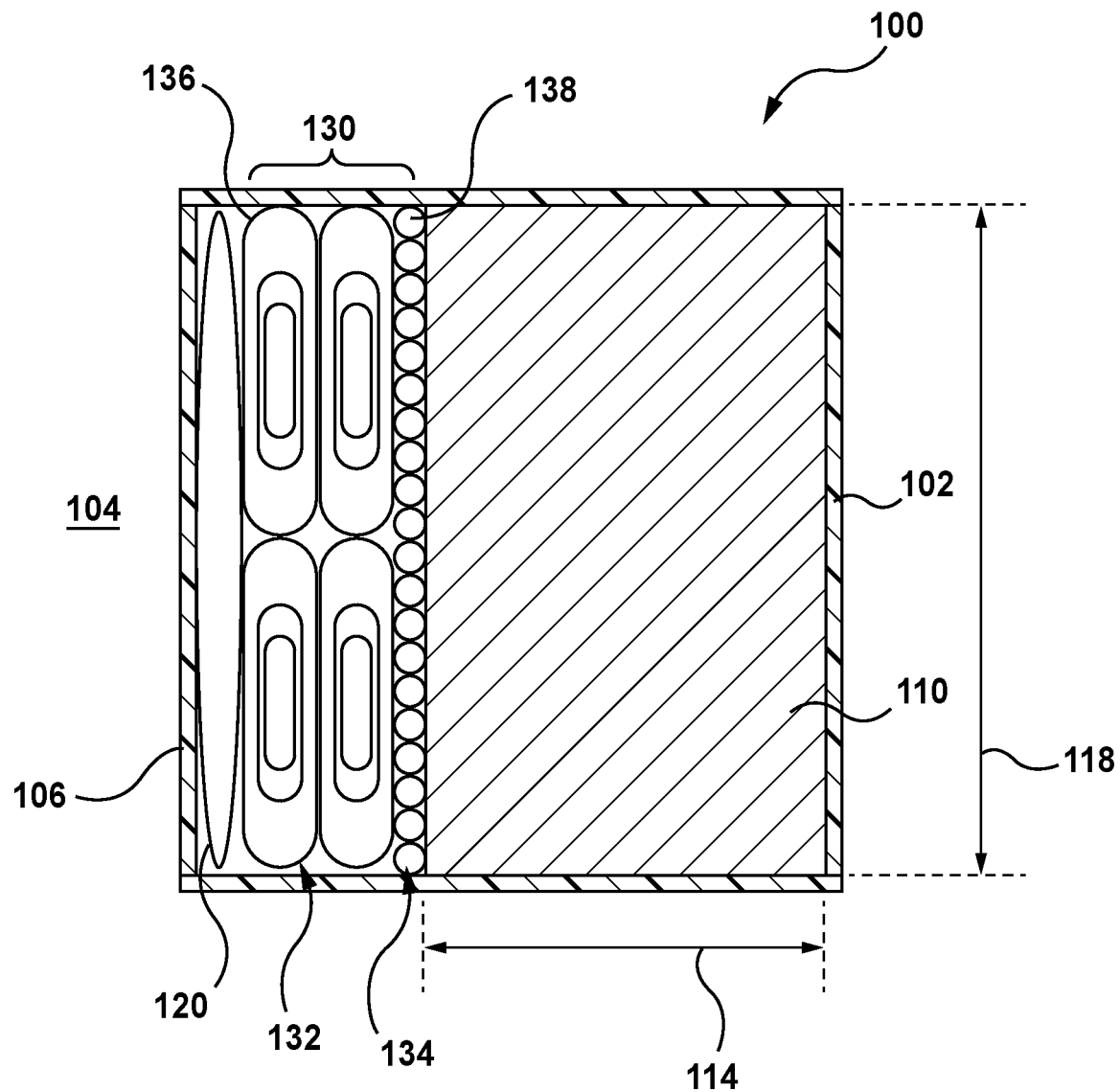
FIG. 3 is a cross-section taken along line 3-3 in FIG. 1.

Referring to FIGS. 2 and 3, in the example shown, the device 100 includes a plurality of magnets 110 within the interior volume 108. In the examples shown, the magnets are arranged around the appendage-receiving bore—i.e. at least a portion of the bore 104 is positioned between at least two of the plurality of magnets 110. The magnets 110 produce a magnetic field in the appendage-receiving bore 104.

In the example shown, the magnets 110 are permanent magnets that are arranged in an annulus around the appendage-receiving bore 104. Specifically, in the example shown, the magnets 110 are shaped as sectors of an arc, and are arranged to form a Halbach array, with the respective magnetic field of each magnet indicated by arrows 112 (shown in FIG. 2), so that a relatively strong magnetic field is produced in the appendage-receiving bore 104, and a relatively weak or zero magnetic field is produced outside of the annulus of magnets 110. The Halbach array may include, for example, between 8 and 32 magnets. In some examples, the Halbach array includes 16 magnets.

The magnets 110 may in some examples be rare-earth magnets, such as neodymium magnets or samarium cobalt magnets. In some examples, the magnets 110 are N-52 or N-55 grade neodymium magnets.

The magnets 110 may, for example, generate a magnetic field in the appendage-receiving bore 104 having a magnetic field strength of less than 1 T. For example, the magnetic field in the appendage-receiving bore 104 may have a magnetic field strength of between 0.05 T and 0.5 T, or between 0.1 T and 0.3 T, or between 0.15 and 0.35 T, or about 0.32 T. The magnetic field serves to polarize nuclear spins within the appendage receiving bore 104.

Referring still to FIGS. 2 and 3, in some examples, the annulus of magnets 110 has a radial wall thickness 114 of, for example, less than 5 mm. For example, the radial wall thickness 114 may be between about 1 mm and 3 mm. In some examples, the annulus of magnets 110 has an inner diameter 116 of, for example, between 10 mm and 40 mm. For example, the inner diameter 116 may be about 20 mm. In some examples, the annulus of magnets 108 has a height 118 of, for example, between 2 mm and 10 mm. For example, the height 118 may be about 5 mm.

In alternative examples (some of which will be described in detail below with reference to FIGS. 5 to 10B), the plurality of magnets may be of another configuration, and/or may be arranged around the appendage receiving bore in another arrangement. For example, the device may include a pair of magnets positioned on opposed sides of the appendage-receiving bore. For further example, the device may include electromagnets instead of or in combination with permanent magnets. For further example, the plurality of magnets may be of another shape other than sectors of an arc, and/or may include additional magnets (e.g. rectangular magnets) interspersed between the magnets that are shaped as sectors of an arc.

Referring still to FIGS. 2 and 3, the device 100 further includes a nuclear magnetic resonance (NMR) transceiver 120 that is supported by the casing 102. In the example shown, the NMR transceiver 120 includes a single transceiver coil that both transmits and receives, and is positioned within the interior volume 108 and adjacent the inner section 106 of the casing 102. The NMR transceiver 120 is positioned to emit radiofrequency (RF) pulses to the appendage-receiving bore 104, and to receive NMR signals from the appendage-receiving bore 104.

In alternative examples, as will be described below, the NMR transceiver can include a transmitter coil and a separate receiver coil. In further alternative examples, the NMR transceiver can include a plurality of transmitter coils, and/or a plurality of receiver coils, and/or a plurality of transceiver coils.

In the example shown, the NMR transceiver 120 includes a surface coil. In alternative examples, as will be described below, the NMR transceiver can include one or more solenoid coils.

The NMR transceiver 120 can be sized and configured to emit radiofrequency pulses to and receive NMR signals from the entire volume of the appendage-receiving bore 104, or only a section of the appendage-receiving bore 104. In the example shown, the device 100 is configured so that the NMR transceiver 120 emits radiofrequency pulses to and receives NMR signals from a section of the appendage-receiving bore (this section can be referred to herein as a 'target section', and is shown schematically in FIG. 2 at reference character 122), and so that in use, the target section 122 is readily positioned within a highly perfused region of a finger. Particularly, referring back to FIG. 1, in the example shown, the device 100 includes a positioning guide 124 for guiding a user in orienting the device 100 at a target orientation. In the example shown, the positioning guide 124 is formed by a flattened and enlarged section of the casing 102. A wearer of the ring may naturally be inclined to (and/or can be instructed to) position this enlarged section on the dorsal surface of the finger. Referring back to FIG. 2, the NMR transceiver 120 is spaced from a centre-point 126 of the positioning guide 124 by a spacing angle 128. The spacing angle 128 can in some examples be between about 45 degrees and about 180 degrees, or between about 80 degrees and about 150 degrees. Because of the spacing angle 128, when the ring is worn with the enlarged section on the dorsal surface of the finger, the target section 122 captures the palmar digital vein of the wearer.

In some examples (not shown), the device can include a suction mechanism to improve perfusion of blood in the target section. For example, the device can include a miniaturized suction cup on the casing adjacent the NMR transceiver.

In other examples, the positioning guide 124 can include another feature instead of or in addition to the enlarged section of the casing. For example, the casing can be relatively symmetrical in shape (i.e. a simple band without any enlarged sections), but can include a jewel or a marking or a stone or another visual feature that serves as a positioning guide.

In other examples, the target section of the appendage-receiving bore can be centred within the appendage-receiving bore, so that the orientation of the device 100 is immaterial.

In some examples, the device can be configured to boost the intensity of the NMR signal received by the NMR transceiver. For example, the device can employ dynamic nuclear polarisation (DNP) to boost the intensity of the NMR signal received by the NMR transceiver. In such examples, the device can include a microwave resonator (e.g. a single sided microwave resonator) supported by the casing. The microwave resonator can rely on free radicals naturally occurring in blood or on artificially generated free radicals. This will be described in further detail below with regards to FIGS. 10A and 10B. In other examples, brute-force hyperpolarization can be used to boost the intensity of the NMR signal received by the transceiver. In such examples, coils (e.g. a high-temperature superconductor coil, together with electric cryocoolers) can be positioned on opposite ends of the target section and can be pulsed to create a strong magnetic field (e.g. 7 T) in the target section prior to obtaining a blood-analyte measurement.

Referring to FIGS. 2 and 3, in the example shown, the device 100 further includes a shim system 130 that is operable to homogenize the magnetic field or a portion thereof (e.g. a portion including the target section 122 of the magnetic field). As used herein, the term 'homogenize' refers to an increase or improvement in the homogeneity of the magnetic flux density within the appendage receiving bore 104 or a portion thereof. The term 'homogenize' does not require that the appendage receiving bore 104 or a portion thereof be made perfectly or entirely homogeneous.

Referring to FIG. 3, in the example shown, the shim system 130 includes both a dynamic shim system 132, and a static shim system 134. The dynamic shim system 132 includes an active shim coil 136 within the interior volume 108 and extending around the appendage-receiving bore 104. As will be described in further detail below, the active shim coil 136 is activatable to homogenize the target section 122 of the magnetic field. The static shim system 134 includes one or more ferromagnetic materials 138 within the interior volume 108, and extending around the appendage-receiving bore 104. In the example shown, both the active shim coil 136 and the ferromagnetic materials 138 are positioned between the inner section of the casing 106 and the annulus of magnets 110.

In alternative examples, the shim system may be of another configuration. For example, a shim system may include only one of a dynamic shim system and a static shim system.

Referring back to FIG. 2, in the example shown, the device 100 further includes a heart phase sensor 140 that is supported by the casing 102. In the example shown, the heart phase sensor 140 is exterior to the casing 102, and joined to the inner section 106 of the casing 102, so that it is within the appendage-receiving bore 104. The heart phase sensor 140, when activated, can sense diastole and systole in a wearer when an appendage of the wearer is received in the appendage-receiving bore 104. The heart phase sensor can be, for example, an LED heart monitor.

Referring still to FIG. 2, the device 100 further includes an electronics assembly 142 within the interior volume 108. In the example shown, the electronics assembly 142 is in communication with the NMR transceiver 120, the heart phase sensor 140, and the shim system 130. As will be described in further detail below, in the example shown, the electronics assembly 142 is operable to activate the NMR transceiver 120 and the active shim coil 136 to homogenize the target section 122 of the magnetic field. The electronics assembly 142 is further operable to receive a heart phase signal from the heart phase sensor 140. The heart phase signal can be indicative of systole or diastole in the wearer. The electronics assembly 142 is further operable to activate the NMR transceiver 120 during diastole to emit a diastolic RF pulse to the target section 122 of the appendage-receiving bore 104, and receive a diastolic NMR signal from the target section 122 of the appendage-receiving bore 104. The electronics assembly 142 is further operable to activate the NMR transceiver 120 during systole to emit a systolic RF pulse to the target section 122 of the appendage-receiving bore 104, and receive a systolic NMR signal from the target section 122 of the appendage-receiving bore. The diastolic NMR signal and the systolic NMR signal can then be processed to calculate the blood analyte concentration of the wearer.

Referring still to FIG. 2, in the example shown, the device further includes a data transmitter 154 within the interior volume 108. The data transmitter 154 is in communication with the electronics assembly 142. The data transmitter 154 can be, for example a Bluetooth transmitter (e.g. a Bluetooth 5.0 transmitter). The data transmitter 154 can communicate signals between the electronics assembly 142 and a secondary device (not shown), such as a smart-phone, a smart-watch, a tablet, a computer, a drug-delivery device, or other device.

Figure 4:
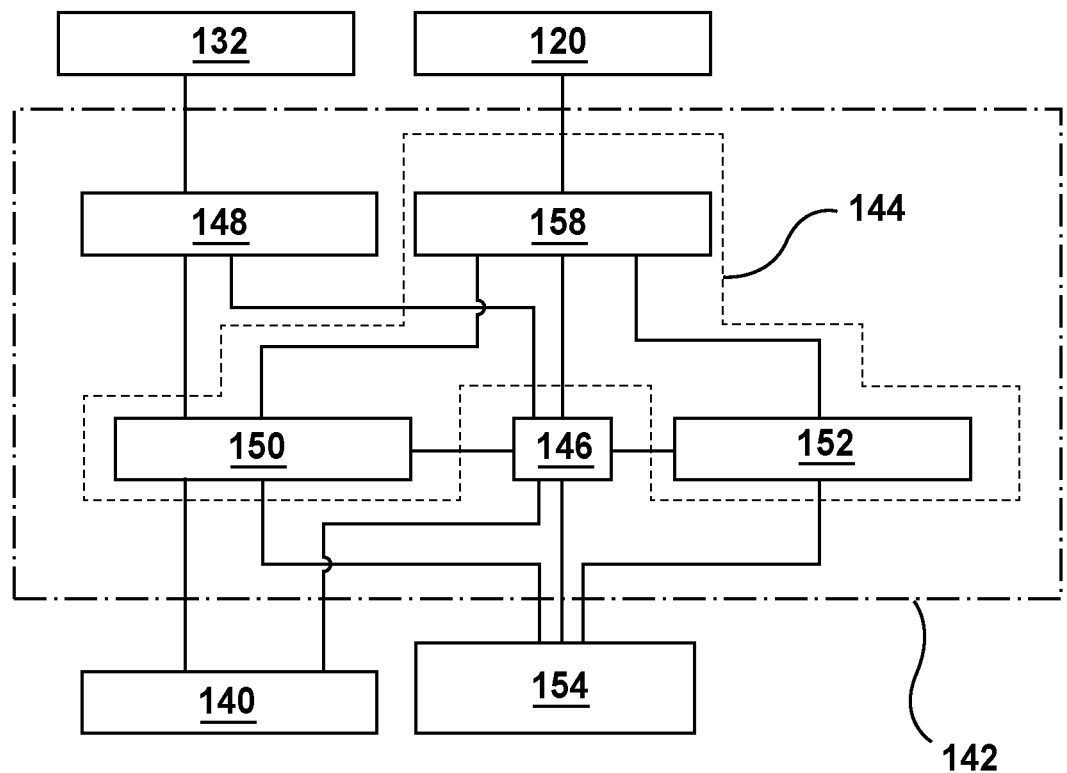
FIG. 4 is a schematic diagram of the electronics assembly of the device of FIG. 1.

Referring to FIG. 4, the electronics assembly 142 and the operation of the device 100 will be described in further detail, by way of example.

In the example shown, the electronics assembly 142 includes an RF control module 144, a central processing unit (CPU) 146, and a shim control module 148. The RF control module 144 is in communication with the NMR transceiver 120 and the CPU 146. Specifically, the RF control module 144 includes an RF transmitter sub-module 150 in communication with the CPU 146, an RF receiver sub-module 152, with quadrature detection, in communication with the CPU 146, and a duplexer 158 in communication with the RF transmitter sub-module 150, the RF receiver sub-module 152, and the NMR transceiver 120. The shim control module 148 is in communication with the CPU 146, the RF control module 144, and the active shim coil 132. The heart phase sensor 140 is in communication with the CPU 146 and with the RF control module 144. The data transmitter 154 is in communication with the CPU 146 and the RF control module 144.

As used herein, the term CPU 146 refers to any unit or module or processor or assembly that can control and/or coordinate other parts of the electronics assembly 142 or the device 100, or can process information received from other parts of the electronics assembly 142 or the device 100.

In some examples, as a first step in measuring the blood analyte concentration, the target section 122 of the appendage receiving bore 104 can be homogenized by a shimming operation. For example, the CPU 146 can signal the RF control module 144 to activate the NMR transceiver 120, which emits a shim pulse to the target section 122. The NMR transceiver 120 can receive a shim signal from the target section 122 of the magnetic field in response to the shim pulse. The RF control module 144 can communicate the shim signal from the NMR transceiver 120 to the CPU 146. The CPU 146 can then activate the shim control module 148 to adjust the current in the active shim coil 132, based on the shim signal. This can be repeated until the CPU 146 determines that the target section 122 is sufficiently homogenized, based on the shim signal. For example, the target section 122 may be considered to be sufficiently homogenized when the field homogeneity is between 0.1 and 1.0 ppm. The shim system can then be "locked".

In alternative examples, rather than the CPU 146 initiating and/or coordinating the shimming operation, the shimming operation can be controlled by the secondary device, via the data transmitter 154.

In some examples, the device can be configured to adjust the NMR frequency in order to account for temperature changes in the plurality of magnets 110. That is, each time an NMR scan is performed, a calibration operation may be performed in order to ascertain the magnetic field strength within the target section 122. The NMR frequency can then be adjusted based on the magnetic field strength.

When the shim is "locked" and the NMR frequency has been adjusted, the device 100 can then perform a "scan" to obtain diastolic and systolic NMR signals. For example, with the heart phase sensor 140 sensing systole and diastole in the wearer, the RF control module 144 can activate the NMR transceiver 120 to emit the diastolic RF pulse and the systolic RF pulse to the target section 122 of the magnetic field, and receive the resulting diastolic NMR signal and systolic NMR signal. Specifically, the CPU 146 can receive the heart phase signal from the heart phase sensor 140, and in response to the heart phase signal, can signal the RF control module 144 to activate the NMR transceiver 120 to emit the diastolic RF pulse during diastole, and the systolic RF pulse during systole. The NMR transceiver 120 can communicate the diastolic NMR signal and the systolic NMR signal to the RF control module 144. Optionally, the device can perform multiple scans in sequence, and provide a blood-analyte concentration based on the multiple scans.

In some examples (not shown), in order to achieve high sensitivity, the number of scans carried out in a given time period can be increased. For example, the device 100 can carry out 128 scans per second or 64 scans per second. In some examples, the scan time can be artificially increased by increasing the number of receiver channels detect the NMR signal. This can be achieved by adding additional receiver coils and preamplifiers to the device.

In alternative examples, rather than the CPU 146 initiating and/or coordinating the scan, the scan can be controlled by the secondary device, via the data transmitter 154.

In some examples, the CPU 146 can then calculate the blood-analyte concentration based on the diastolic NMR signal and the systolic NMR signal. Briefly, the diastolic NMR signal and the systolic NMR signal can be processed to obtain a diastolic NMR spectrum and a systolic NMR spectrum, respectively. This can be achieved by first carrying out signal processing and denoising. For example, the free induction decay signal can be weighted to improve the signal to noise ratio or resolution, a reference deconvolution algorithm can be performed, and/or a denoising algorithm using wavelets can be performed. Then, Fourier transform and quantification can be performed. For example, a Fourier transform of the free induction decay can be performed to generate the NMR spectra. In each spectrum, the area under the analyte peak can be compared to the area under the water peak, to determine the analyte concentration. The systolic analyte concentration can then be subtracted from the diastolic concentration, to determine the blood analyte concentration. This can be done using various signal processing and calculating algorithms, which can be programmed into the software of the CPU 146. The CPU 146 can then communicate the blood-analyte concentration to the data transmitter 154. The data transmitter 154 can then transmit the blood-analyte concentration to the secondary device. The secondary device can have a display, and can then display the blood-analyte concentration.

In other examples, the RF control module and/or the CPU can communicate the diastolic NMR signal and the systolic NMR signal to the data transmitter 154. The data transmitter 154 can then transmit the diastolic NMR signal and the systolic NMR signal to the secondary device, and the secondary device can calculate and optionally display the blood analyte concentration.

In further examples (not shown), the device can include a display, and the device can display the blood-analyte concentration.

In some examples, the electronics assembly 142 (or parts thereof) may be provided on an ASIC (application specific integrated circuit) chip (not shown).

The blood-analyte concentration can optionally be calculated and displayed periodically, optionally at regular intervals, while the device 100 is worn. Alternatively, the blood-analyte concentration can be calculated and displayed or upon receiving a request from a wearer. The request from the wearer can optionally be input into the secondary device and transmitted from the secondary device to the device 100, or can be input directly into the device 100. Optionally, the device 100 can include an alarm function, which can be triggered when the calculated blood analyte concentration is above a set value, or can trigger an alarm function in the secondary device.

Referring back to FIG. 2, in the example shown, the device 100 further includes a power source 156 that powers the various parts of the device 100 (e.g. the NMR transceiver 120, the electronics assembly 142, the shim system 130, the data transmitter 154, and the heart-phase monitor 140). The power source 156 can be a rechargeable battery, optionally an inductively rechargeable battery. The device 100 can optionally be sold in a kit with a charger (not shown), optionally an inductive charger, for the battery. The device 100 can optionally be worn on a daily basis, and can be removed nightly for charging. Depending on the frequency at which the diastolic and systolic NMR signals are obtained, the battery may last for between 4 hours and 72 hours on a single charge.

In some examples (not shown), in order to decrease noise in the NMR signal, the device can include an electric cryocooler for supercooling the receiver coil.

Figure 5:
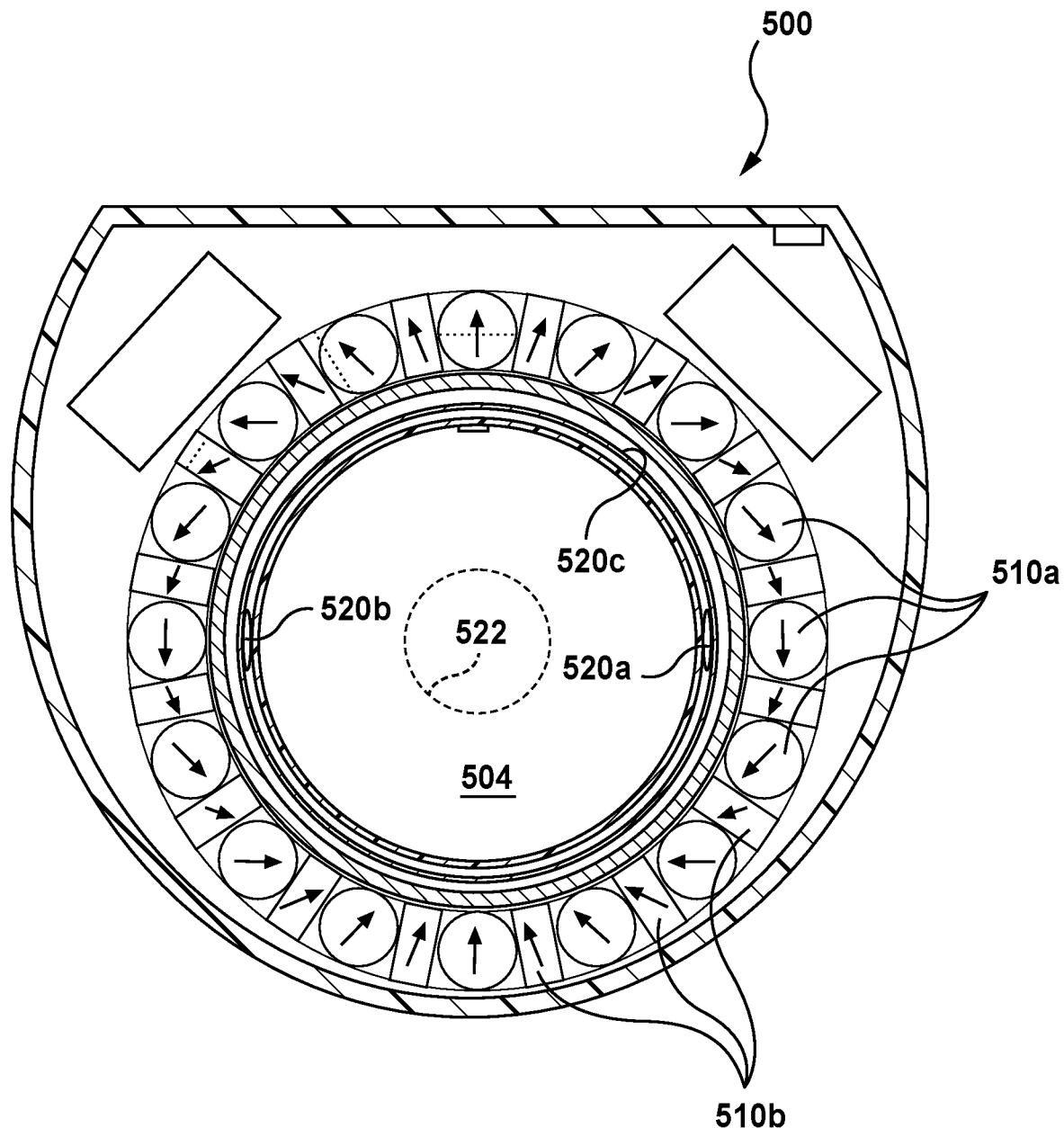
FIG. 5 is a cross-section taken through an alternative wearable blood analyte measurement device.

Referring now to FIG. 5, an alternative device 500 is shown. In FIG. 5, elements that are like those of FIGS. 1 to 4 are referred to with like reference numerals, incremented by 400. In the example of FIG. 5, the device 500 is similar to the device 100; however, the device 500 includes a plurality of cylindrical magnets 510a and a plurality of rectangular bar magnets 510b, arranged in an alternating pattern. The magnets 510a and 510b are oriented to produce a dipole magnetic field within the bore 504 of the device.

Figure 6:
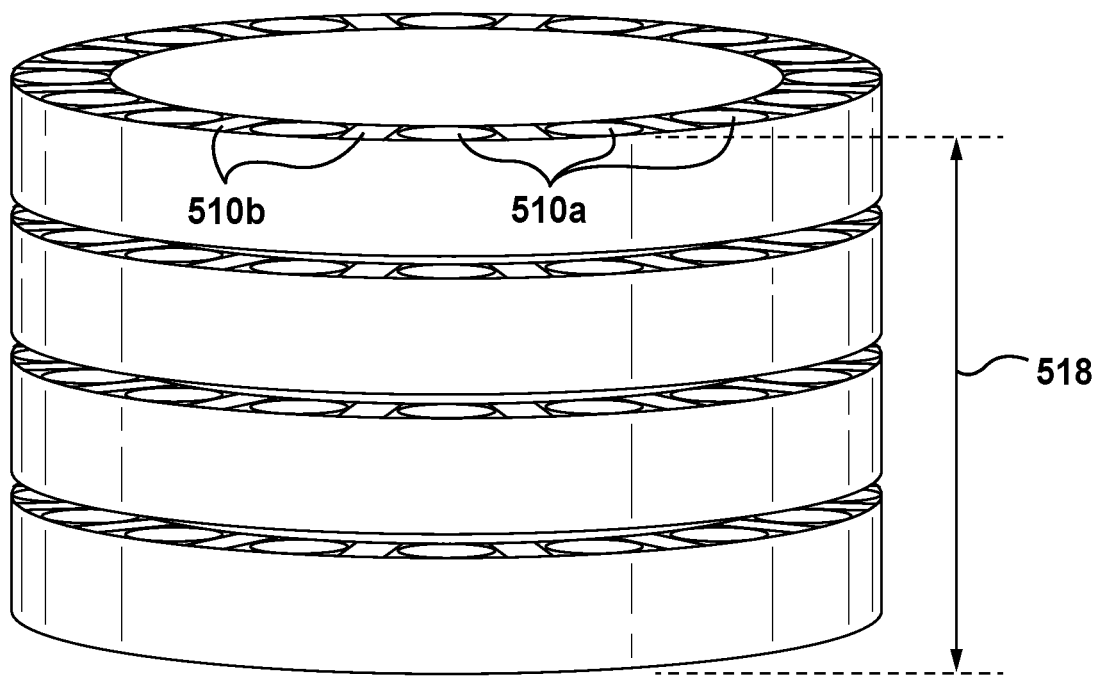
FIG. 6 is a perspective view of the plurality of magnets of the device of FIG. 5.

Referring to FIG. 6 (wherein the magnets 510a and 510b are shown separately from the device), in the example shown, the device 500 includes a plurality of annular rows of magnets 510a and 510b. The use of rows can reduce magnetic field inhomogeneities. In the example shown, 4 rows of magnets are used; however, in alternative examples, another number of rows could be used.

In the example shown, the device 500 includes 16 cylindrical magnets 510a and 16 bar magnets 510b in each row; however, in alternative examples, another number of each type of magnet could be used. In some examples, the combined height 518 of the rows can be between 2 mm and 20 mm. For example, the height 518 may be about 10 mm.

During manufacture of the device 500, the cylindrical magnets 510a can be rotated about their longitudinal axis, and the bar magnets 510b can be shifted slightly radially inward or outward, to adjust the local magnetic field. Furthermore, the rows of magnets can be rotated to adjust the local magnetic field.

Furthermore, in the example of FIG. 5, the NMR transceiver includes a pair of surface coils 520a, 520b for receiving NMR signals, and a solenoid coil 520c for transmitting RF pulses. In this example, the target section 522 can be centrally located within the appendage receiving bore 504.

Figure 7:
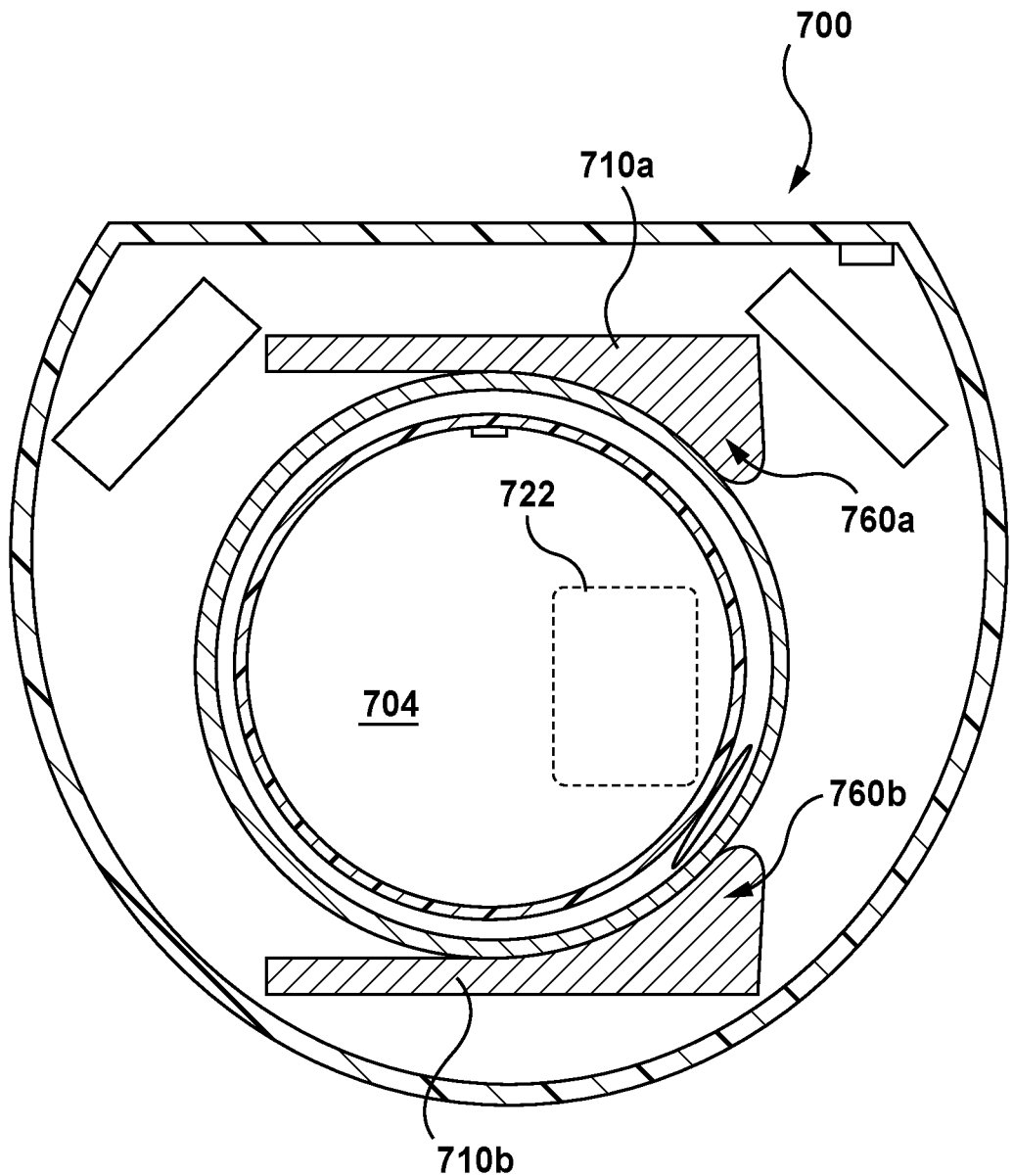
FIG. 7 is a cross-section taken through another example wearable blood analyte measurement device.

Referring now to FIG. 7, an alternative device 700 is shown. In FIG. 7, elements that are like those of FIGS. 1 to 4 are referred to with like reference numerals, incremented by 600. In the example of FIG. 7, the device 700 is similar to the device 100; however, the device 500 includes a pair of magnets 710a, 710b, on opposed sides of the appendage receiving bore 704. The magnets 710a, 710b each have an enlarged region 760a, 760b, which produces a strong and relatively homogeneous magnetic field in target section 722.

Figure 8:
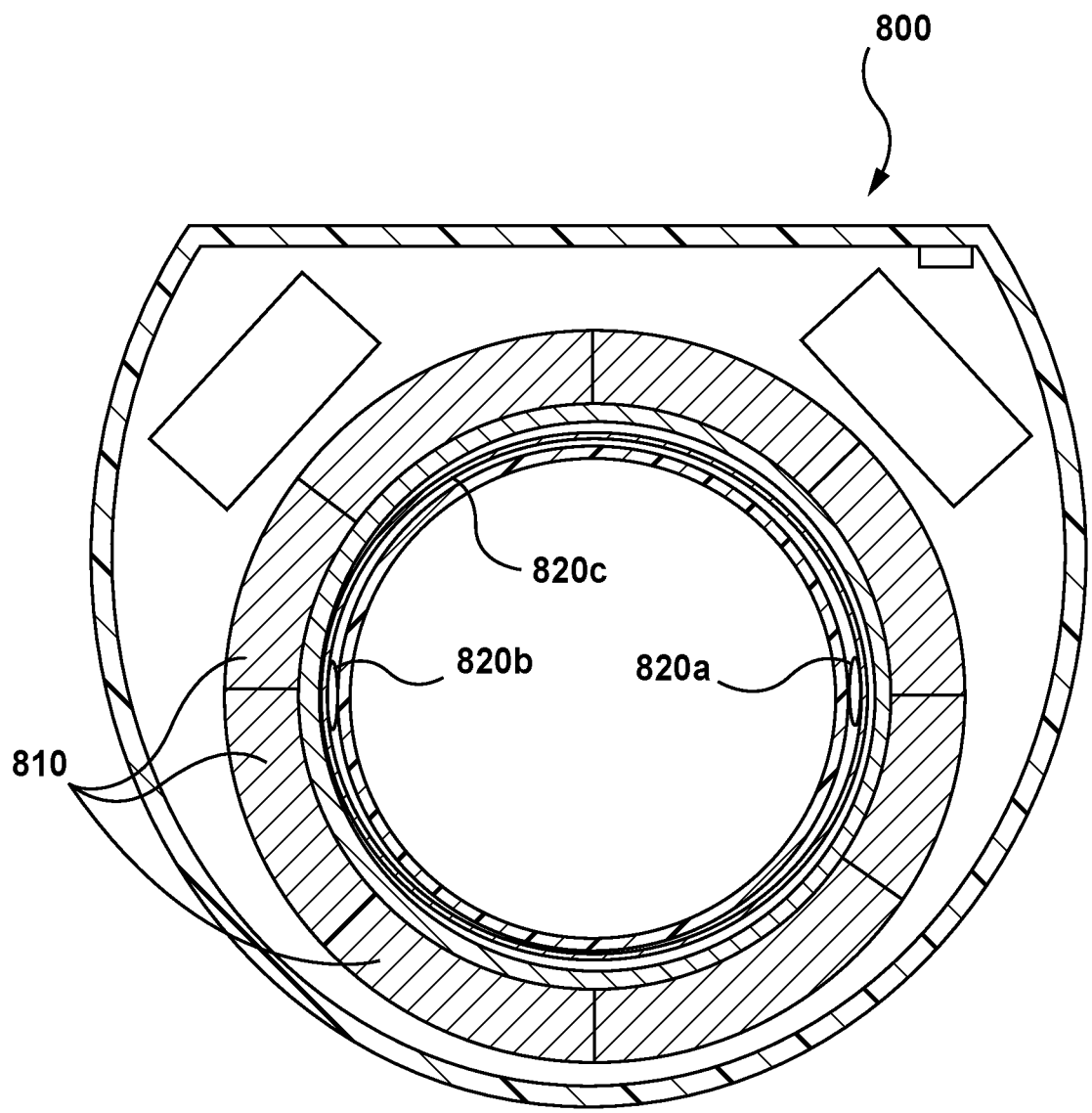
FIG. 8 is a cross-section taken through another example wearable blood analyte measurement device.

Referring now to FIG. 8, another alternative device 800 is shown. In FIG. 8, elements that are like those of FIGS. 1 to 4 are referred to with like reference numerals, incremented by 700. In the example of FIG. 8, the device 800 is similar to the device 100; however, the device includes 8 magnets 810 in a Hallbach array, and the NMR transceiver includes a pair of surface coils 820a, 820b for receiving NMR signals, and a solenoid coil 820c for transmitting RF pulses. Furthermore, the device 800 does not include a heart phase monitor. Instead, the concentration of an analyte in the wearer's blood (as opposed to other tissues) is measured by taking advantage of unique nuclear magnetic resonance properties of blood.

In some examples, the device can be configured to take advantage of the T2/T1 ratio of blood (where T2 refers to the spin-spin relaxation time and T1 refers to the spin-lattice relaxation time). That is, blood has a relatively high T2/T1 ratio, as compared to other tissues. Balanced Steady State Fee Precession (b-SSFP) pulse sequences are sensitive to tissues/molecules with a high T2/T1 ratio. Accordingly, the solenoid coil 820c can emit rapid repeated pulses with a constant repetition time to generate a b-SSFP signal, in order to isolate the NMR signal from the blood in the target section. In such examples, since fat can also have a relatively high T2/T1 ratio, a fat suppression pulse may also be employed.

Alternatively or in addition, the device can be configured to take advantage of the relatively high T2 signal of blood. That is, blood gives a relatively high T2 signal, as compared to other tissues. Accordingly, the solenoid coil 820c can emit a CPMG spin echo train, which can include an initial excitation at the Ernst angle, and repeated 180 degree pulses with a constant repetition time, in order to obtain the T2 signal from the target section. A T2 filter can then be employed (e.g. in the electronics assembly or in the secondary device), to filter out relatively low T2 signals (e.g. signals with a T2 of less than 15 ms), leaving only the T2 signal from blood.

Figure 9:
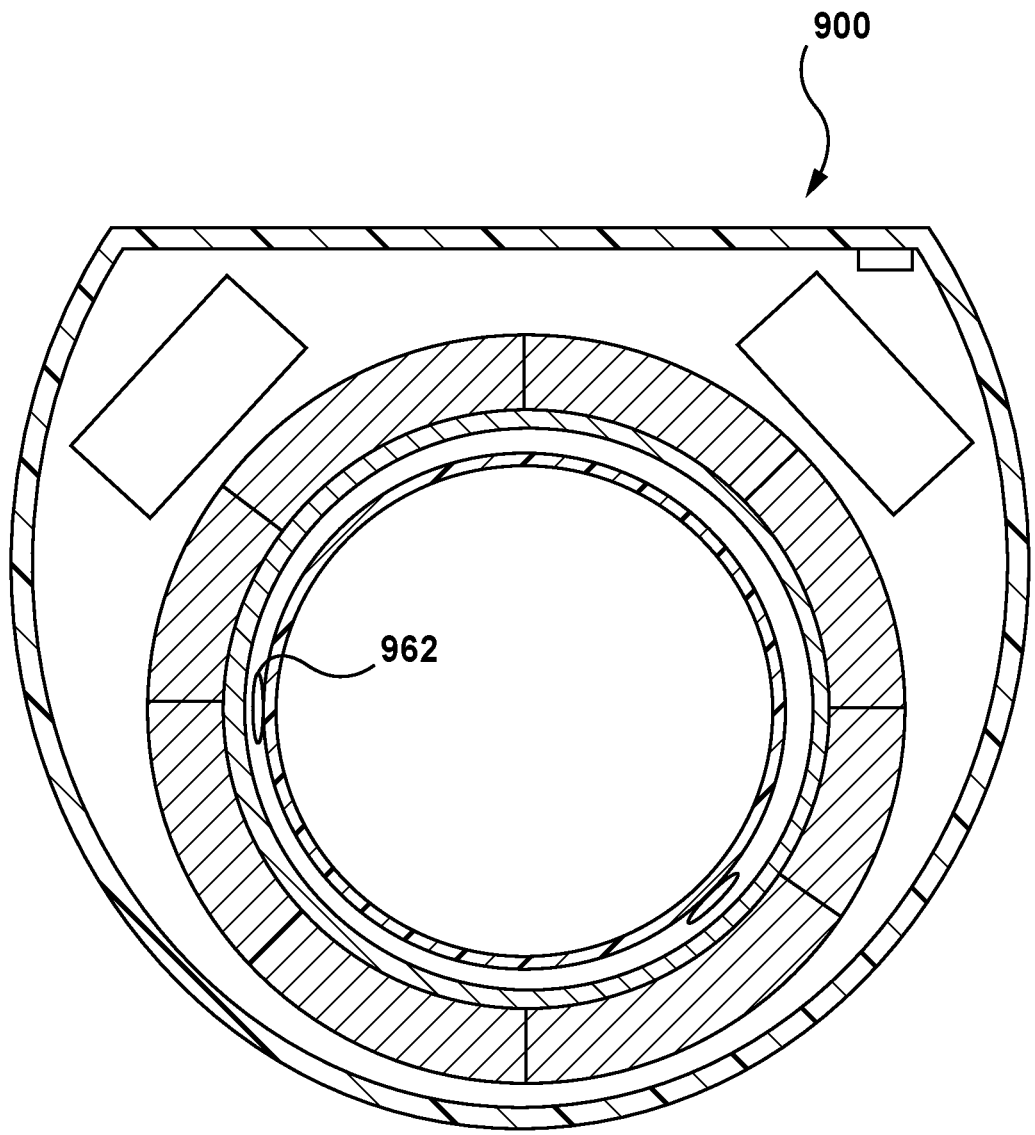
FIG. 9 is a cross-section taken through another example wearable blood analyte measurement device.

Referring now to FIG. 9, another alternative device 900 is shown. In FIG. 9, elements that are like those of FIGS. 1 to 4 are referred to with like reference numerals, incremented by 800. In the example of FIG. 9, similarly to device 800, the device 900 does not include a heart phase monitor. Instead, the device 900 includes a gradient coil 962, and takes advantage of the fact that blood will be flowing through the target section, whereas other tissues will be stationary. The gradient coil can refocus the spin of the moving blood, while the spin from stationary tissues will remain unfocused, so that the NMR signal from the blood is isolated.

In alternative examples, the device can include additional gradient coils, such as a total of 2 gradient coils or 3 gradient coils.

Figure 10A:
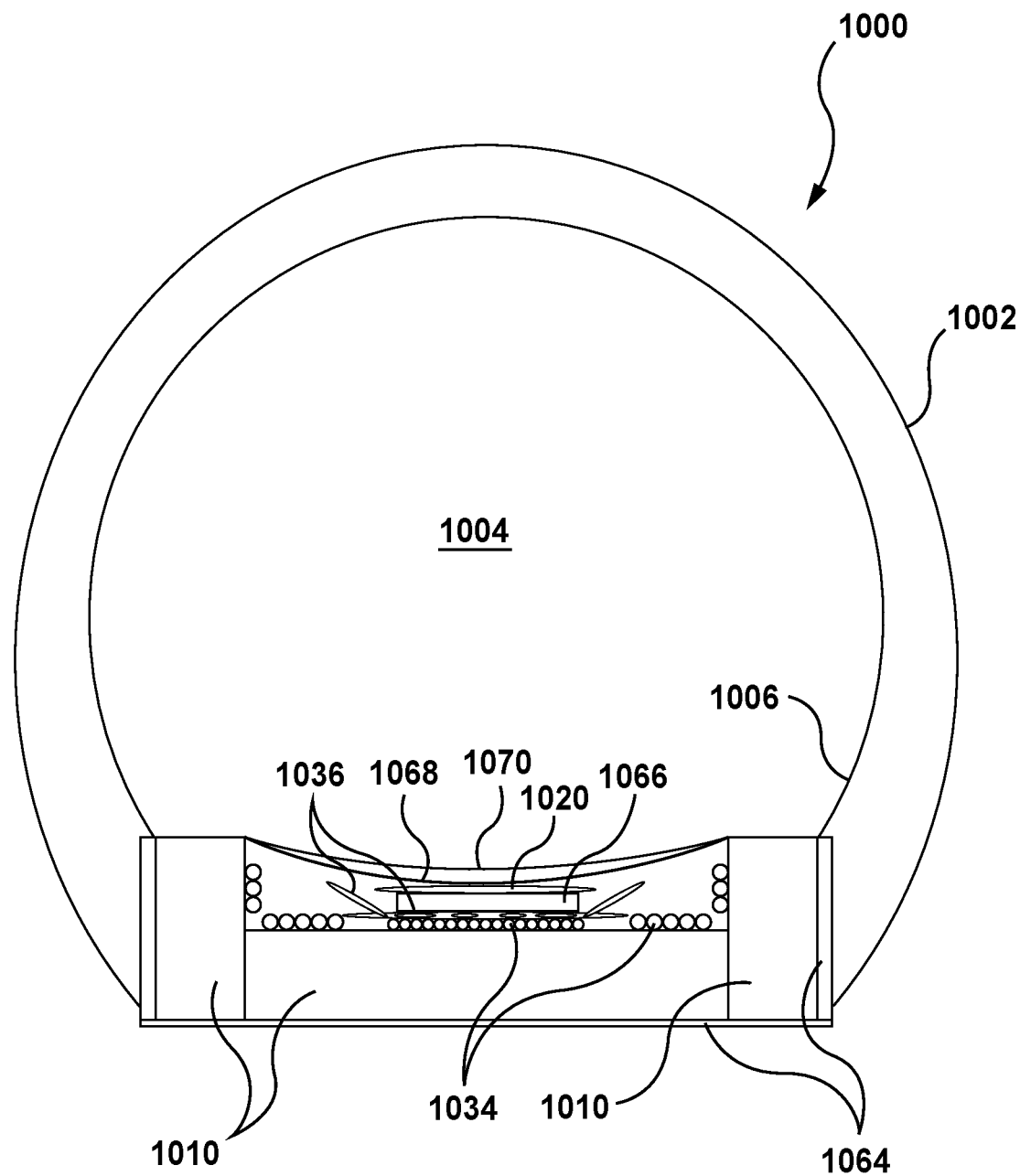
FIG. 10A is a cross-section taken through another example wearable blood analyte measurement device.
Figure 10B:
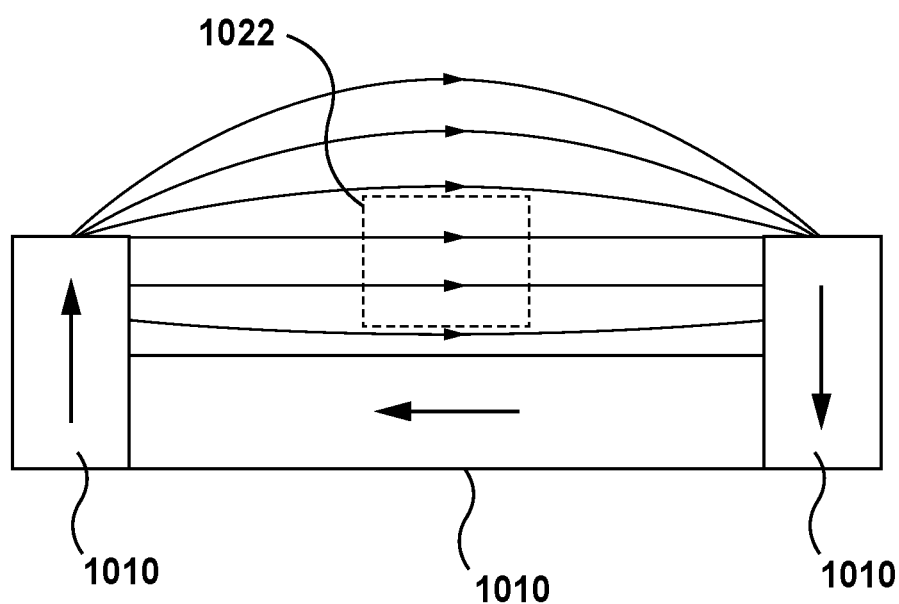
FIG. 10B is an enlarged view of a portion of the device of FIG. 10A.

Referring now to FIGS. 10A and 10B, another alternative device 1000 is shown. In FIGS. 10A and 10B, elements that are like those of FIGS. 1 to 4 are referred to with like reference numerals, incremented by 900. In the example of FIGS. 10A and 10B, the device 1000 includes three magnets 1010, which are positioned on only one side of device 1000, in a generally U-shaped configuration, to create a target section 1022 (shown in FIG. 10B) adjacent the magnets 1010 and within the U-shape. A material 1064 that provides magnetic shielding and thermal insulation can line the magnets 1010. Furthermore, the device 1000 is configured to employ DNP to boost the intensity of the NMR signal received by the NMR transceiver. That is, the device includes a microwave resonator 1066, and a capacitive micromachined ultrasonic transducer array 1068, which are housed in the casing 1002, adjacent the NMR transceiver 1020, active shim coils 1036 and the passive shimming materials 1034. A solid ultrasound coupling medium 1070 is provided on the inner section 1006 of the casing 1002. The ultrasonic transducer array 1068 can be used to generate free radicals in the blood, by sonolysis. This can result in polarization transitions. The microwave resonator 1066 can then transmit a microwave signal to the bore, 1004 to transfer the polarization to 1H spins, in order to boost the intensity of the NMR signal.

In some examples (not shown), a laser pulse can be used to create cavitation nuclei, which can facilitate sonolysis.

Figure 11:
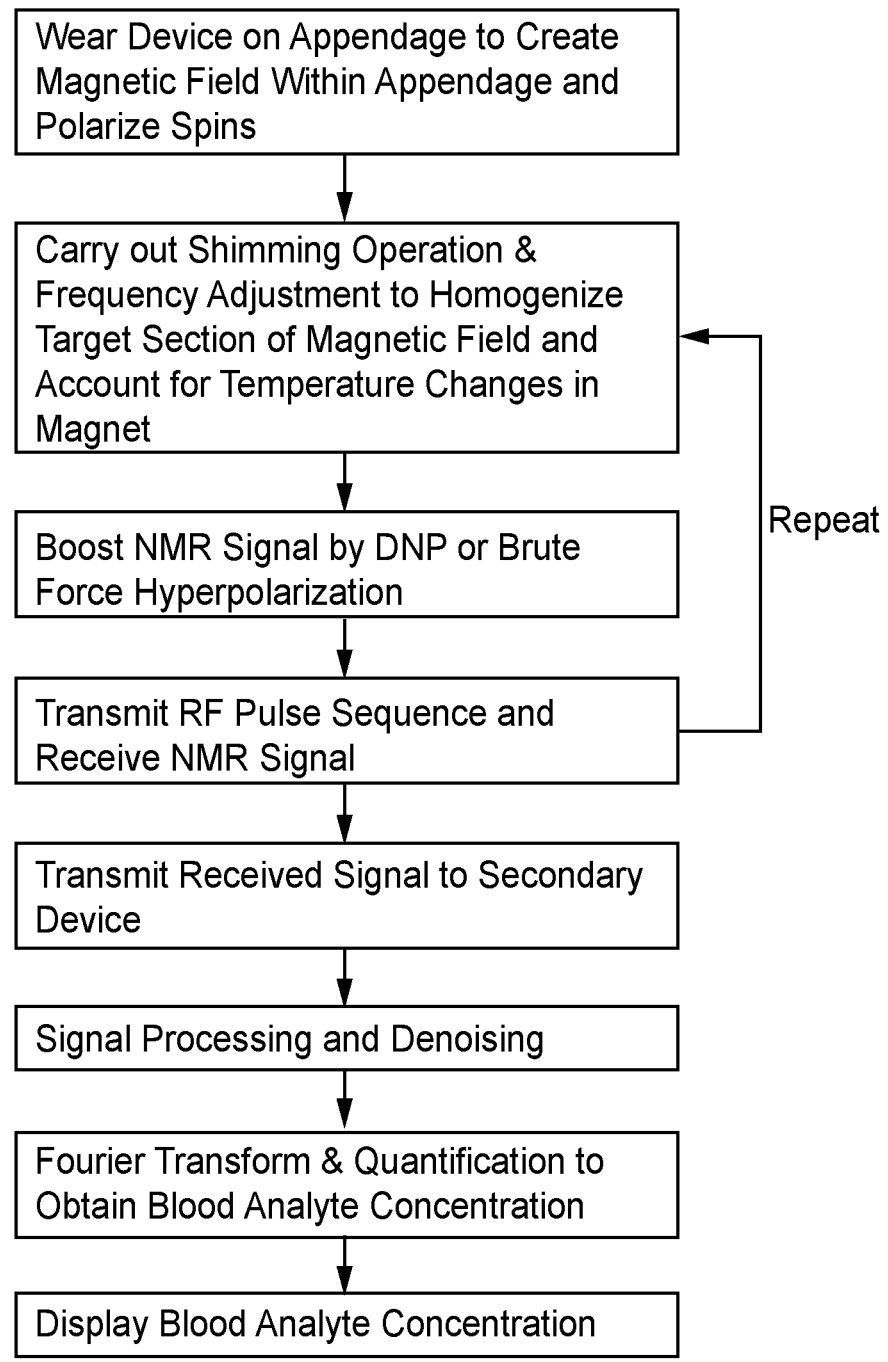
FIG. 11 is a flowchart showing a general example of the operation of the devices described herein.

A summary flowchart of the general operation of the devices described above is shown in FIG. 11.

As used herein, the term "NMR signal" can refer to an unprocessed NMR signal, such as an analog NMR signal, or a processed NMR signal, such as a digital NMR signal (e.g. resulting from processing of an analog NMR signal).

While the above description provides examples of one or more processes or apparatuses, it will be appreciated that other processes or apparatuses may be within the scope of the accompanying claims.

To the extent any amendments, characterizations, or other assertions previously made (in this or in any related patent applications or patents, including any parent, sibling, or child) with respect to any art, prior or otherwise, could be construed as a disclaimer of any subject matter supported by the present disclosure of this application, Applicant hereby rescinds and retracts such disclaimer. Applicant also respectfully submits that any prior art previously considered in any related patent applications or patents, including any parent, sibling, or child, may need to be re-visited.

We claim:

1. A system, comprising:

a casing defining an appendage-receiving bore;

a plurality of magnets supported by the casing, the magnets producing a magnetic field in the appendage-receiving bore, wherein the plurality of magnets are arranged along an arcuate portion about the appendage-receiving bore, wherein the plurality of magnets comprises magnets shaped as sectors of an arc, wherein the plurality of magnets comprises magnets configured to be shifted radially inward;

a transmitter supported by the casing, wherein the transmitter is configured to periodically excite an appendage within the appendage-receiving bore throughout a time period of at least 4 hours;

a receiver supported by the casing and positioned to receive a nuclear magnetic resonance (NMR) signal from the appendage; and a processing system in communication with the transmitter and the receiver, wherein the processing system is configured to determine a blood analyte concentration based on the NMR signal.

2. The system of claim 1, wherein the system is wearable, wherein the casing is configured to retain the system on the appendage, wherein the transmitter is configured to periodically excite the appendage throughout the time period while the system is worn on the appendage.

3. The system of claim 1, wherein the transmitter is activated at intervals throughout the time period.

4. The system of claim 1, wherein the NMR signal is one of a set of NMR signals received by the receiver throughout the time period, wherein the processing system is configured to determine a blood analyte concentration for each of the set of NMR signals.

5. The system of claim 4, wherein each blood analyte concentration is calculated based on multiple NMR signals in the set of NMR signals.

6. The system of claim 1, wherein the receiver comprises a surface coil.

7. The system of claim 6, wherein the appendage comprises a finger, wherein the surface coil is positioned to emit a radiofrequency (RF) signal towards a palmar surface of the finger.

8. The system of claim 1, further comprising a positioning guide coupled to the casing, wherein the positioning guide is configured to facilitate a target orientation for the casing relative to the appendage.

9. The system of claim 1, wherein an asymmetric geometry of the appendage-receiving bore facilitates a target orientation for the casing relative to the appendage.

10. The system of claim 9, wherein the appendage comprises a finger, wherein the receiver is positioned on a palmar side of the appendage when the casing is positioned in the target orientation.

11. The system of claim 1, wherein the processing system comprises an electronics assembly within an interior volume of the casing, wherein processing system is configured to activate the transmitter to excite the appendage.

12. The system of claim 11, wherein the processing system is activated in response to a request.

13. The system of claim 1, wherein the processing system is configured to determine the blood analyte concentration using a T2 filter.

14. The system of claim 1, wherein exciting the appendage within the appendage-receiving bore comprises emitting a radiofrequency (RF) signal towards the appendage-receiving bore, wherein the RF signal comprises a fat suppression pulse.

15. The system of claim 1, wherein the time period is at least one day.

16. The system of claim 1, wherein the appendage comprises a finger, wherein the NMR signal is received from a target section of the finger, wherein the target section comprises a palmar region of the finger.

17. The system of claim 1, further comprising a gradient coil supported by the casing.

18. The system of claim 1, wherein the magnetic field is less than 1 Tesla.

19. The system of claim 1, wherein the blood analyte concentration comprises glucose concentration.

* * * * *